(12) United States Patent
Remondini

(10) Patent No.: US 10,859,548 B2
(45) Date of Patent: Dec. 8, 2020

(54) METHOD AND DEVICE FOR THE ANALYSIS OF A GAS SAMPLE

(71) Applicant: SACMI COOPERATIVA MECCANICI IMOLA SOCIETA' COOPERATIVA, Imola (IT)

(72) Inventor: Marco Remondini, Imola (IT)

(73) Assignee: SACMI COOPERATIVA MECCANICI IMOLA SOCIETA' COOPERATIVA, Imola (IT)

(*) Notice: Subject to any disclaimer, the term of this patent is extended or adjusted under 35 U.S.C. 154(b) by 0 days.

(21) Appl. No.: 16/435,185

(22) Filed: Jun. 7, 2019

(65) Prior Publication Data

US 2019/0285598 A1   Sep. 19, 2019

Related U.S. Application Data

(62) Division of application No. 15/100,924, filed as application No. PCT/IB2014/066521 on Dec. 2, 2014, now Pat. No. 10,338,045.

(30) Foreign Application Priority Data

Dec. 2, 2013 (IT) .............................. BO2013A0671

(51) Int. Cl.
G01N 33/00 (2006.01)

(52) U.S. Cl.
CPC ..... *G01N 33/0022* (2013.01); *G01N 33/0001* (2013.01)

(58) Field of Classification Search
CPC ....................... G01N 33/0022; G01N 33/0001

USPC ......................................................... 73/23.34
See application file for complete search history.

(56) References Cited

U.S. PATENT DOCUMENTS

| 5,265,031 A | * | 11/1993 | Malczewski ....... G01N 33/0022 |
| | | | 702/24 |
| 2005/0061056 A1 | | 3/2005 | Sunshine et al. |
| 2008/0210089 A1 | | 9/2008 | Tsangaris et al. |

FOREIGN PATENT DOCUMENTS

| EP | 0488120 | 6/1992 |
| EP | 2352024 | 8/2011 |
| WO | 2012083432 | 6/2012 |

OTHER PUBLICATIONS

International Search Report for PCT/IB2014/066521 dated Feb. 13, 2015.
U.S. Appl. No. 15/100,924, Jul. 18, 2018, Office Action.
U.S. Appl. No. 15/100,924, Feb. 15, 2019, Notice of Allowance.

* cited by examiner

*Primary Examiner* — John Fitzgerald
*Assistant Examiner* — Rodney T Frank
(74) *Attorney, Agent, or Firm* — Workman Nydegger

(57) ABSTRACT

Method and device for the analysis of a gas sample; the method provides for the sample to be conveyed from an inlet along a feeding duct and from the feeding duct, divided into equal portions, along a plurality of passage channels and through a plurality of detecting stations; in the area of each detecting station a sensor is arranged, which detects a different characteristic of the sample; the gas sample portions are conveyed directly and precisely onto the sensors so as to increase the speed and sensitivity of the detection.

5 Claims, 5 Drawing Sheets

METHOD AND DEVICE FOR THE ANALYSIS OF A GAS SAMPLE

CROSS REFERENCE TO RELATED APPLICATIONS

This application is a divisional of U.S. application Ser. No. 15/100,924, filed on Jun. 1, 2016, which is a 371 Application of PCT Patent Application No. PCT/IB2014/066521, filed on Dec. 2, 2014, which claims priority to Italian Application No. BO2013A000671, filed Dec. 2, 2013, the entireties of which are incorporated herein by reference.

TECHNICAL FIELD

The present invention concerns an analysis method, an analysis device and an analysis unit.

BACKGROUND TO THE INVENTION

The use of the present invention is particularly suited to application in the detection of odours and in the field of so-called electronic noses, to which the following description specifically refers without loss of generality.

In the field of odour detection, devices are known comprising an analysis chamber inside which, in the area of a base wall, a plurality of sensors are arranged, each of which is adapted to detect a different characteristic of a gaseous sample. In use, the gaseous sample is conveyed through the relatively large analysis chamber above the sensors and tangentially to the sensors themselves.

EP488120 discloses a process for the continuous analysis of contaminants of a gas. A sample of the gas is passed through a plurality of analysers.

WO2012/083432 discloses methods for detecting at least one odour in a gas sample. For example, in one method the sample is passed inside a thermal conditioning chamber so as to control the temperature of the gas sample; the sample is brought into contact with different sensors.

US2005/061056 discloses a device for detecting vapours, said device being sufficiently lightweight and small to be hand-held.

EP2352024 discloses a sensor similar to a cartridge and formed of a housing having a base and a cover fixed to the base and provided with an inlet opening, an outlet hole and a channel for the gas to be analysed extending between the inlet opening and the outlet hole.

Devices of the type described above, although accurate, have a relatively low speed and sensitivity.

Aim of the present invention is to provide an analysis method, an analysis device and an analysis unit which allow the drawbacks of the known art to be overcome, at least partially, and at the same time are easy and inexpensive to produce.

SUMMARY

According to the present invention, an analysis method, an analysis device and an analysis unit are provided as claimed in the following independent claims and, preferably, in any one of the claims depending directly or indirectly on the independent claims.

BRIEF DESCRIPTION OF THE FIGURES

The invention is described below with reference to the accompanying drawings, which illustrate non-limiting embodiment examples thereof, in which.

DETAILED DISCLOSURE

Figure 1:
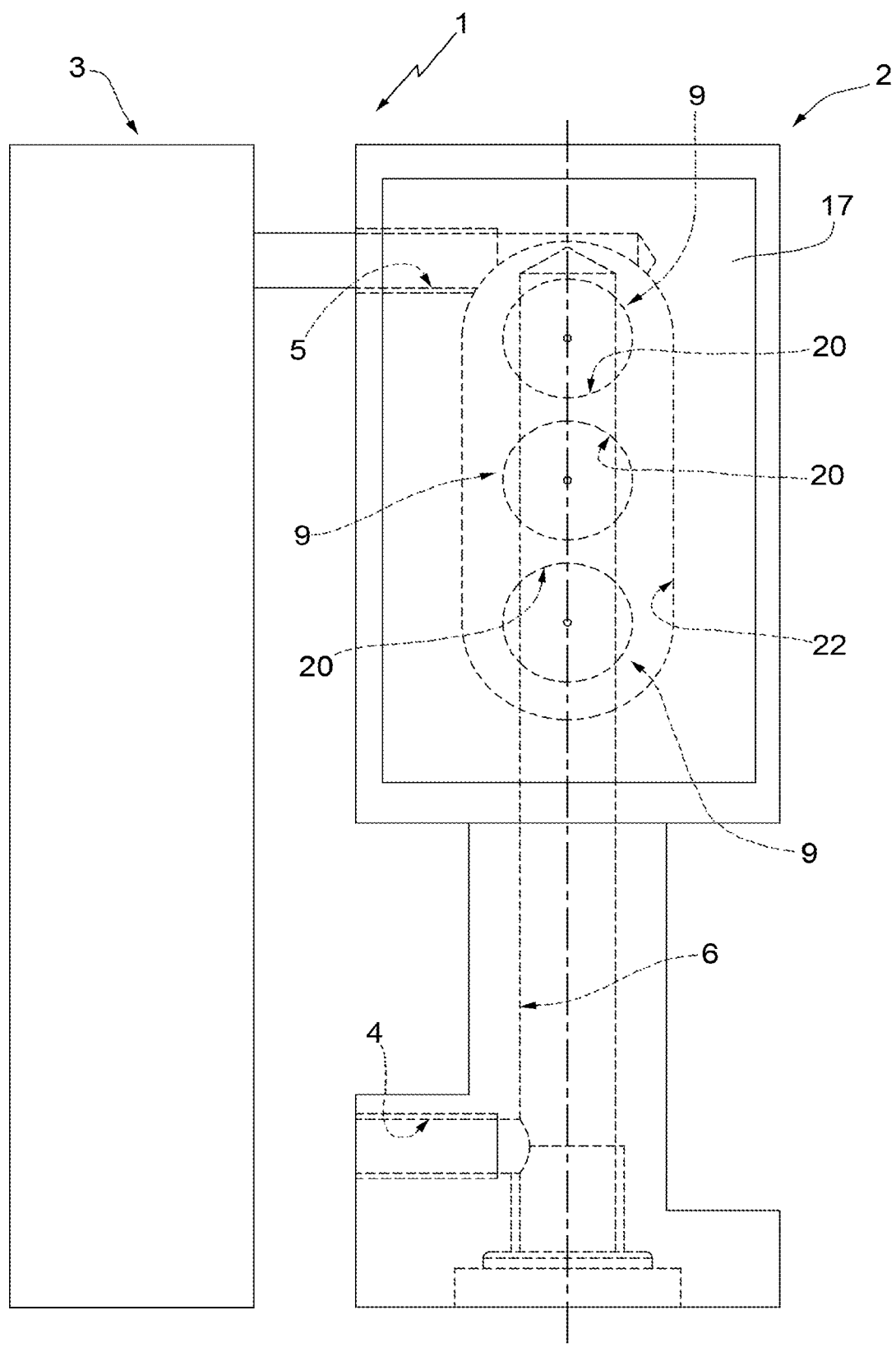
FIG. 1 is a frontal view of a device according to the present invention.

In FIG. 1, according to a first aspect of the present invention, the number 1 indicates as a whole an analysis device for the analysis of a gas sample. The device 1 comprises an analysis unit 2 and a movement unit 3 for conveying the gas sample through the analysis unit 2.

Figure 2:
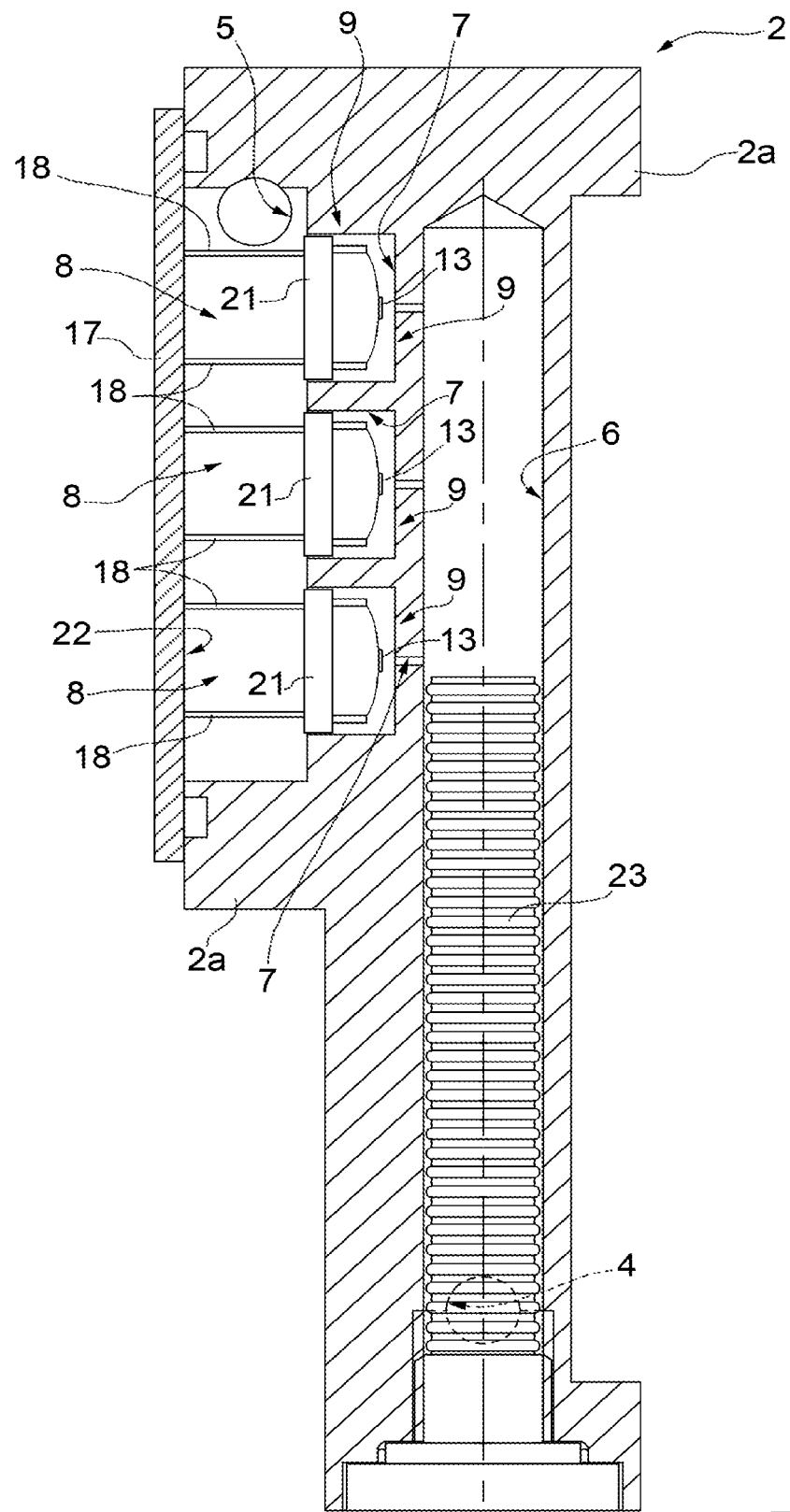
FIG. 2 is a section according to the line I-I of the device of FIG. 1.

With particular reference to FIG. 2, the analysis unit 2 comprises an inlet 4 for letting the gas sample into the analysis unit 2; an outlet (in particular, to allow the gas sample to leave the analysis unit 2); a feeding duct 6, which is arranged downstream of the inlet 4 (with respect to a feed direction of the gas sample); and at least two (in the present case three) passage channels 7, which are arranged downstream (with respect to a feed direction of the gas sample) of the feeding duct 6 and upstream (with respect to a feed direction of the gas sample) of the outlet 5.

The analysis unit 2 further comprises at least two (in the present case three) sensors 8, each of which is arranged in the area of a respective detecting station 9 positioned along a relative passage channel 7 upstream of the outlet 5.

The movement unit 3 is adapted to convey the gas sample from the inlet 4 to the outlet 5, along a given path. In particular, the movement unit 3 is adapted to convey the gas (more precisely, the gas sample) from the inlet 4, along the feeding duct 6, through the passage channels 7, through the detecting stations 9, to said outlet 5.

Each passage channel 7 comprises a respective segment 10, which is arranged between the feeding duct 6 and the relative detecting station 9. Each passage channel 7 is adapted to allow the movement of a respective portion of the gas sample from the feeding duct 6 (in particular, through the respective segment 10 and the relative detecting station 9) to the relative sensor 8.

In this way, in use, each portion of the gas sample is passed, separately from the others and in a controlled manner, through the respective detecting station 9. Furthermore, the entire gas sample (or at least the majority of it) passes through the area of the sensors 8.

Advantageously, each segment 10 has a cross section substantially constant (equal) throughout its longitudinal extension. In this way, the gas coming out of each segment 10 moves, in use, according to a substantially laminar flow.

Each segment 10 extends from the feeding duct 6 to the respective detecting station 9.

According to some embodiments, each passage channel 7 extends from the feeding duct 6 transversally to the feeding duct 6 itself. More precisely, the passage channels 7 are arranged in sequence along the longitudinal extension of the feeding duct 6.

In particular, each channel 7 is delimited (closed) along the lateral perimeter and has one end 11 open on the duct 6 and one end 12 open opposite the end 11. More precisely, each channel 7 is defined by a respective through hole through the wall laterally delimiting the duct 6.

In this regard, it should be noted that, according to some embodiments, the duct 6 does not have further openings in addition to the inlet 4 and the holes defining the channels 7.

More precisely, the duct 6 has two closed ends and is laterally delimited by the above cited wall.

Figure 3:
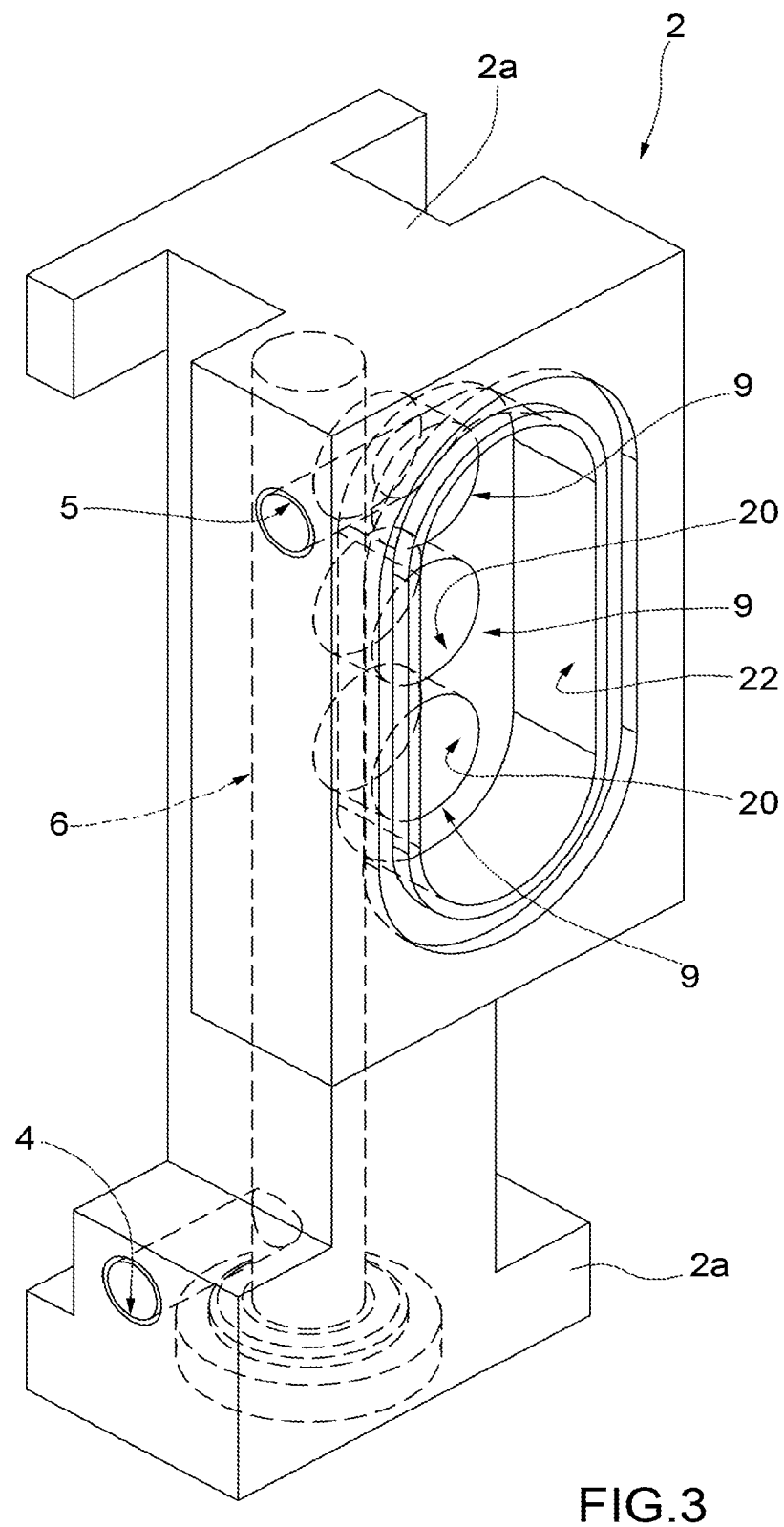
FIG. 3 is a perspective view of a part of the device of FIG. 1 with some details removed for clarity.

With reference to the depicted embodiment (in particular, see FIG. 3), it should be noted that the analysis unit 2 comprises a main body 2a (in one piece) in which the passage channels 7 and the feeding duct 6 are obtained.

With particular reference to FIG. 1, the movement unit 3 comprises (in particular, is) a sucking device (more precisely, a pump), which is arranged downstream of the detecting stations to convey the gas sample portions through the detecting stations 9 (and through the outlet 5).

In this way, it has been experimentally observed that the portions of the gas sample are conveyed to the area of the sensors in a reliable and substantially constant manner. This results in improved sensitivity and higher detection speed.

According to some embodiments, the sensors 8 are selected from the group consisting of: sensors adapted to detect a specific substance, metal oxide sensors (MOS—for example, such as those produced by the company Figaro—http://www.figaro.co.jp) and a combination thereof.

In particular, the sensors 8 (FIGS. 2 and 4) adapted to detect a specific substance are electrochemical sensors (for example, those produced by the company Figaro).

Advantageously, each sensor 8 is adapted to detect a different characteristic of the sample. In this way and using MOS type sensors, it is possible to use the device 1 as an electronic nose adapted to identify different odours.

Figure 4:
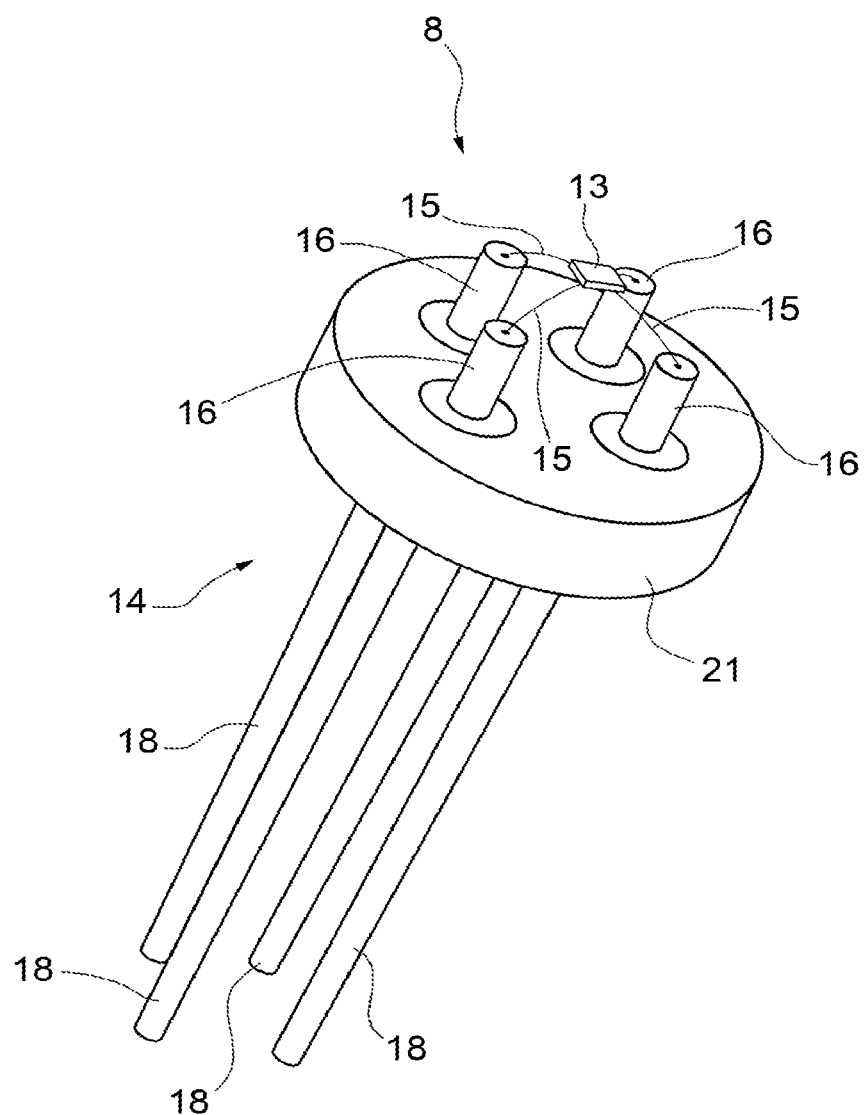
FIG. 4 is a perspective schematic view of a detail of the device of FIG. 1.

With particular reference to FIG. 4, each sensor 8 comprises a respective sensitive element 13, which is adapted to interact (in particular, come into contact) with a gas (in particular, the respective portion of the gas sample) to detect a characteristic thereof (for example, the concentration of a given component and/or the response to a particular stress).

According to some embodiments, the sensitive element 13 is of the type described in the patent application with publication number WO2004/095013.

Each sensor 8 further comprises a case 14, on which the sensitive element 13 is mounted by means of respective gold wires 15. In particular, the gold wires 15 join the sensitive element 13 to rheophores 16 of the case 14.

According to some embodiments, the case 14 is of the TO39 type.

The sensors 8 are mounted on a common printed circuit 17 by means of terminals 18 made of conductive material (for example gilded iron).

Figure 5:
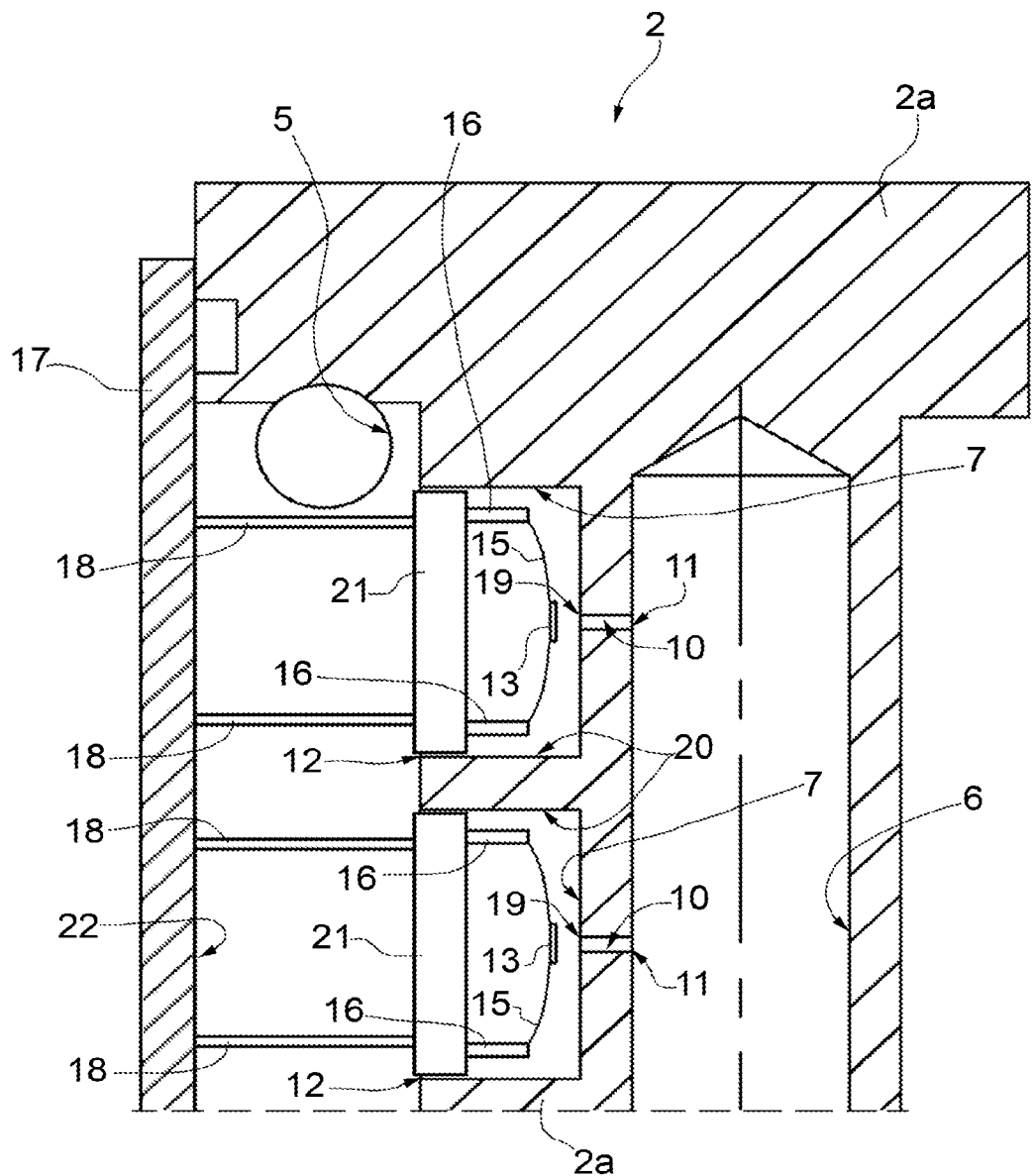
FIG. 5 illustrates a part of FIG. 2 on an enlarged scale.

With particular attention to FIG. 5, advantageously, each sensitive element 13 (more precisely, an active surface thereof) is arranged in the area of an end opening 19 of the respective segment 10 opposite the feeding duct 6. In particular, each sensitive element 13 (more precisely, its active surface) faces the relative end opening 18 of the respective segment 10.

Advantageously, the end opening 19 has an area smaller than or equal (in particular, smaller) to the area of the sensitive element 13 (more precisely, of its active surface). More precisely, the sensitive element 13 (in particular, its active surface) completely covers the end opening of 19 (in the direction of forward movement of the gas along the segment 10 and, in particular, in the direction of forward movement of the gas coming out of the segment 10 through the end opening 18).

According to specific embodiments, the sensitive element 13 (more precisely, its active surface) has an area of at least 0.5 $mm^2$. In particular, the sensitive element 13 has an area up to 5 $mm^2$.

In particular, each passage channel 7 has an alveolus 20 presenting an inner cross section with area greater than the area of the respective segment 10. Each alveolus 20 delimits a respective detecting station 9 and houses a relative sensor 5. Each alveolus 20 has a first end coupled to the respective segment 10 and a second end, which is opposite to the first end and in the area of which a supporting element 21 of the respective sensor 8 (more precisely, of the case 14) is arranged. Each supporting element 21 is closed (in other words, it cannot be crossed by gas).

More in particular, each supporting element 21 is mounted in contact with the inner surface of the respective alveolus 20 but so as to allow the passage of gas between the supporting element 21 and the alveolus 20. In other words, each supporting element 21 is arranged in the respective alveolus 20 not in a fluid-tight manner.

Advantageously, the sensitive element 13 is oriented so that the relative portion of the gas sample conveyed along the respective passage channel 7 comes into contact with the sensitive element 13 moving in a direction transverse (in particular, substantially perpendicular) to the sensitive element 13 (more precisely to its active surface).

According to some embodiments, the analysis unit 2 comprises a confluence chamber 22, which is adapted to collect the gas passed through (all) the detecting stations 9. In particular, the confluence chamber 22 is arranged downstream of the detecting stations 9 (and of the sensors 8) and upstream of the outlet 5.

It should be noted that the confluence chamber 22 is delimited on the opposite side with respect to the passage channels 7 by the printed circuit 17. Advantageously, the printed circuit 17 is closed (in other words, it cannot be crossed by gas). The printed circuit 17 is mounted in a fluid-tight manner on the main body 2a of the analysis unit 2.

Advantageously, each passage channel 7 has a respective volumetric flow rate substantially equal to the volumetric flow rates of the other passage channels 7. In particular, each segment 10 has a respective inner cross section with an area substantially equal to the areas of the inner cross sections of the other segments 10.

In this way, the gas sample portions that reach each sensor 8 are substantially equal to one another.

According to specific embodiments, each segment 10 has a respective inner cross section with an area of approximately 0.2 $mm^2$ to approximately 0.78 $mm^2$. In some particular cases, each segment 10 has a respective inner cross section with area of approximately 0.2 $mm^2$.

Advantageously, the feeding duct 6 has an inner cross section with an area at least one hundred times the area of the inner cross section of each segment 10.

According to specific embodiments, the feeding duct 6 has an inner cross section with an area of approximately 110 $mm^2$ to approximately 180 $mm^2$. According to some embodiments, the feeding duct 6 has a length of approximately 60 mm to approximately 90 mm.

In this way, it is possible to reduce (substantially cancel) the pressure loss between the passage channels 7.

Advantageously, the feeding duct 6 has an inner cross section with an area at least ten times, in particular at least fifteen times, the square of the length of each segment 10.

According to some embodiments, each segment 10 has a length of approximately 1 mm to approximately 3 mm.

Advantageously, each segment 10 has an inner cross section with an area of at least one sixteenth of the square of the length of the segment 10 itself.

These aspects allow reduction of the pressure loss along each segment 10 and therefore allow the gas sample portions to reach the sensors 8 (more precisely, their sensitive elements 13) in a particularly efficient manner.

According to some embodiments, the analysis unit 2 also comprises a mixing element 23, which is adapted to determine turbulence in the gas (in particular, in the gas sample) passing through the feeding duct 6. The turbulence allows improved transfer of heat between the walls of the duct 6 (in particular, the main body 2*a*) and the gas. The turbulence also improves the homogeneity of the gas sample.

The element 23 has a substantially cylindrical shape, extends longitudinally inside the feeding duct 6 and has its own first end in the area of the inlet 4 and a second end opposite the first end immediately upstream of the passage channels 7.

The outer surface of the element 23 has substantially the shape of a sinusoid (three-dimensional) which extends along the longitudinal extension of the element 23. In particular, the element 23 appears as a sequence of toroidal elements (without their through hole) positioned one on another.

In accordance with a second aspect of the present invention, an analysis unit is provided as defined above.

In accordance with a third aspect of the present invention, a method is provided for analysis of a gas sample by means of an analysis unit 2 comprising a feeding duct 6; at least two passage channels 7; and at least two sensors 8, each of which is arranged in the area of a respective detecting station 9 along a relative passage channel 7. Each passage channel 7 comprises a respective segment 10, which is arranged between the feeding duct 6 and the relative detecting station 9.

In particular, the analysis unit 2 is as defined above according to the second aspect of the present invention. More in particular, the mentioned method is implemented by means of an analysis device 1 comprising the analysis unit 2 and a gas moving unit 3. More in particular, the device 1 is as defined according to the first aspect of the present invention.

The method comprises a step of conveying the gas sample along the feeding duct 6; a step of bringing at least two portions of the gas sample from the feeding duct 6, each, along a respective passage channel 7 (through a respective segment 10 and through a respective detecting station 9) to a respective sensor 8; and a detecting step, during which each sensor 8 performs a detection operation on the respective portion of the gas sample. In particular, during the step of conveying the two portions of the gas sample, each portion is fed through the detecting station 9 by means of suction due to a sucking device arranged downstream of the detecting stations 9.

According to some embodiments, each sensor 8 detects a different characteristic of the sample.

Advantageously, each sample portion is conveyed according to a substantially laminar flow against a respective sensitive element 13 of the relative sensor 8.

Advantageously, each sample portion is conveyed against a respective sensitive element 13 of the relative sensor 8 in a transverse direction (in particular, substantially perpendicular) to the sensitive element 13 (more precisely, to its active surface).

The sample portions are conveyed along each passage channel 7 with flow rates substantially equal to one another.

In particular, the combination of the portions constitutes the gas sample.

Advantageously, the gas sample is conveyed along the duct 6 with a turbulent motion.

The invention claimed is:

1. A method for the analysis of a gas sample by means of an analysis device for the analysis comprising a feeding duct, at least two passage channels, and at least two sensors, each of which is arranged at a respective detecting station along a relative passage channel, each passage channel comprising a respective segment, which is arranged between the feeding duct and the respective detecting station, the method comprising:
   a step of conveying the gas sample along the feeding duct;
   a step of conveying each one of at least two portions of the gas sample from the feeding duct along a respective passage channel and through the respective detecting station, each respective portion being fed through the respective detecting station by means of suction due to a sucking device arranged downstream of the detecting stations; and
   a detecting step, during which each sensor performs a detection on the respective portion of the gas sample, wherein each sensor has its own sensitive element, which is oriented in such a way that the respective portion of the gas sample conveyed along the relative passage channel comes into contact with the sensitive element while moving in a direction transverse to the sensitive element.

2. A method according to claim 1, wherein each sample portion is conveyed against a respective sensitive element of the relative sensor according to a substantially laminar flow.

3. A method according to claim 1, wherein each sample portion is conveyed against a respective sensitive element of the relative sensor in a direction that is substantially perpendicular to the sensitive element.

4. A method according to claim 1, wherein the sample portions are conveyed along each passage channel with flow rates that are substantially equal to one another, the combination of the portions making up the gas sample.

5. A method according to claim 1, wherein each sensor detects a characteristic of the sample that is different from the characteristics detected by the other sensors.

* * * * *